United States Patent
Bae et al.

(10) Patent No.: US 11,872,032 B2
(45) Date of Patent: Jan. 16, 2024

(54) APPARATUS AND METHOD FOR ESTIMATING ANALYTE CONCENTRATION

(71) Applicant: SAMSUNG ELECTRONICS CO., LTD., Suwon-si (KR)

(72) Inventors: Sang Kon Bae, Seongnam-si (KR); So Young Lee, Daejeon (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 1040 days.

(21) Appl. No.: 16/740,989

(22) Filed: Jan. 13, 2020

(65) Prior Publication Data
US 2020/0261003 A1    Aug. 20, 2020

(30) Foreign Application Priority Data
Feb. 19, 2019    (KR) .................. 10-2019-0019074

(51) Int. Cl.
*G01N 33/48* (2006.01)
*G01N 33/50* (2006.01)
(Continued)

(52) U.S. Cl.
CPC ........ *A61B 5/14532* (2013.01); *A61B 5/7203* (2013.01); *G06F 17/153* (2013.01);
(Continued)

(58) Field of Classification Search
CPC . A61B 5/14532; A61B 5/7203; G06F 17/153; G06F 17/18; G16B 40/10; G01N 21/359
See application file for complete search history.

(56) References Cited

U.S. PATENT DOCUMENTS

| 6,876,931 B2 | 4/2005 | Lorenz et al. |
| 7,436,511 B2 | 10/2008 | Ruchti et al. |

(Continued)

FOREIGN PATENT DOCUMENTS

| JP | 2003-42948 A | 2/2003 |
| JP | 2011-92613 A | 5/2011 |
|    | (5360718 |  |

(Continued)

OTHER PUBLICATIONS

Vrabie et al. Independent component analysis of Raman spectra: Application on paraffin-embedded skin biopsies. Biomedical Signal Processing and Control, vol. 2, pp. 40-50. (Year: 2007).*

(Continued)

*Primary Examiner* — Russell S Negin
(74) *Attorney, Agent, or Firm* — Sughrue Mion, PLLC

(57) ABSTRACT

A method of estimating a concentration of an analyte may include obtaining a plurality of in vivo estimation spectra, generating a plurality of noise detection models by varying a number of principal components based on the plurality of in vivo estimation spectra, comparing the generated plurality of noise detection models with a plurality of concentration estimation models for each number of principal components, extracting a noise spectrum and a concentration estimation model for use in estimating the concentration of the analyte based on the comparison, updating the extracted concentration estimation model based on the extracted noise spectrum, and estimating the concentration of the analyte by using the updated concentration estimation model and an in vivo estimation spectrum from among the plurality of in vivo estimation spectra.

20 Claims, 11 Drawing Sheets

(51) Int. Cl.
  A61B 5/145    (2006.01)
  G06F 17/18    (2006.01)
  G06F 17/15    (2006.01)
  A61B 5/00     (2006.01)
  G16B 40/10    (2019.01)
  G01N 21/31    (2006.01)
  G01N 21/359   (2014.01)

(52) U.S. Cl.
  CPC ............ *G06F 17/18* (2013.01); *G16B 40/10* (2019.02); *G01N 21/359* (2013.01); *G01N 2021/3155* (2013.01)

(56) References Cited

U.S. PATENT DOCUMENTS

| 7,438,855 | B2 | 10/2008 | Sota et al. |
| 7,756,558 | B2 | 7/2010 | Ridder et al. |
| 8,010,299 | B2 | 8/2011 | Arnvidarson |
| 2003/0031597 | A1 | 2/2003 | Sota et al. |
| 2006/0167348 | A1 | 7/2006 | Arnold et al. |
| 2017/0079565 | A1 | 3/2017 | Choi et al. |
| 2017/0319185 | A1 | 11/2017 | Choi et al. |
| 2018/0146899 | A1 | 5/2018 | Lee et al. |

FOREIGN PATENT DOCUMENTS

| KR | 10-2017-0035675 A | 3/2017 |
| KR | 10-2017-0126310 A | 11/2017 |
| KR | 10-2018-0061959 A | 6/2018 |

OTHER PUBLICATIONS

Saptari et al., "Measurements and quality assessments of near-infrared plasma glucose spectra in the combination band region using a scanning filter spectrometer", Journal of Biomedical Optics, vol. 10, No. 6, 2005, 10 pages total.

Sun, "Comparison and combination of near-infrared and Raman spectra for PLS and NAS quantitation of glucose, urea and lactate", University of Iowa, Dec. 2013, 90 pages total.

* cited by examiner

APPARATUS AND METHOD FOR ESTIMATING ANALYTE CONCENTRATION

CROSS-REFERENCE TO RELATED APPLICATION(S)

This application is based on and claims priority under 35 U.S.C. § 119 to Korean Patent Application No. 10-2019-0019074, filed on Feb. 19, 2019, in the Korean Intellectual Property Office, the disclosure of which is incorporated by reference herein in its entirety.

BACKGROUND

1. Field

The disclosure relates to an apparatus and method for estimating the concentration of an in vivo analyte from a bio-signal.

2. Description of Related Art

Diabetes is a chronic disease that causes various complications and is difficult to cure, such that people with diabetes are advised to check their blood glucose regularly to prevent complications. In particular, when insulin is administered to control blood glucose levels, the blood glucose levels should be closely monitored to avoid hypoglycemia and control insulin dosage. An invasive method of finger pricking is generally used to measure blood glucose levels. However, while the invasive method may provide high reliability in measurement, it may cause pain and inconvenience as well as an increased risk of disease or infections due to the use of injection. Recently, research has been conducted on methods of non-invasively measuring blood glucose by using a spectrometer without blood sampling.

SUMMARY

Provided is an apparatus and method for estimating the concentration of an in vivo analyte from a bio-signal.

Additional aspects will be set forth in part in the description which follows and, in part, will be apparent from the description, or may be learned by practice of the presented embodiments.

According to an aspect of the disclosure, a method of estimating a concentration of an analyte may include obtaining a plurality of in vivo estimation spectra, generating a plurality of noise detection models by varying a number of principal components based on the plurality of in vivo estimation spectra, comparing the generated plurality of noise detection models with a plurality of concentration estimation models for each number of principal components, extracting a noise spectrum and a concentration estimation model for use in estimating the concentration of the analyte based on the comparison, updating the extracted concentration estimation model based on the extracted noise spectrum, and estimating the concentration of the analyte by using the updated concentration estimation model and an in vivo estimation spectrum from among the plurality of in vivo estimation spectra.

The obtaining of the plurality of in vivo estimation spectra may include obtaining the in vivo estimation spectra by receiving the plurality of in vivo estimation spectra from an external device, or by measuring the plurality of in vivo estimation spectra by emitting light towards an object and receiving light reflected by or scattered from the object.

The generating of the plurality of noise detection models by varying the number of principal components may include extracting a predetermined number of principal component spectra by analyzing the plurality of in vivo estimation spectra.

The extracting of the predetermined number of principal component spectra may include extracting the predetermined number of principal component spectra by using one of Principal Component Analysis (PCA), Independent Component Analysis (ICA), Non-negative Matrix Factorization (NMF), and Singular Value Decomposition (SVD).

The extracting of the noise spectrum and the concentration estimation model for use in estimating the concentration of the analyte may include determining a correlation coefficient for each number of principal components by comparing the generated plurality of noise detection models with the plurality of concentration estimation models for each number of principal components, determining a number of principal components having a correlation coefficient which is less than or equal to a predetermined threshold value, or a correlation coefficient which has a greatest variation, extracting a principal component spectrum, corresponding to the determined number of principal components, as the noise spectrum from among the predetermined number of principal component spectra, and extracting a concentration estimation model, corresponding to the determined number of principal components, as the concentration estimation model for use in estimating the concentration of the analyte from among the plurality of concentration estimation models.

The estimating of the concentration of the analyte may include selecting an in vivo spectrum, which is a most recently measured spectrum, from among the plurality of in vivo estimation spectra.

The analyte may be at least one of glucose, triglyceride, urea, uric acid, lactate, protein, cholesterol, or ethanol.

The method may include obtaining a plurality of in vivo training spectra which are measured in a predetermined interval, and generating the plurality of concentration estimation models by varying a number of principal components based on the obtained plurality of in vivo training spectra.

The predetermined interval may be an interval in which the concentration of the analyte of an object is substantially constant.

The analyte may be glucose, and the interval, in which the concentration of the analyte of the object is substantially constant, may be a fasting interval.

According to an aspect of the disclosure, an apparatus for estimating a concentration of an analyte may include a processor configured to obtain a plurality of in vivo estimation spectra, generate a plurality of noise detection models by varying a number of principal components based on the plurality of in vivo estimation spectra, compare the generated plurality of noise detection models with a plurality of concentration estimation models for each number of principal components, extract a noise spectrum and a concentration estimation model for use in estimating the concentration of the analyte based on the comparison, update the extracted concentration estimation model based on the extracted noise spectrum, and estimate the concentration of the analyte by using the updated concentration estimation model and an in vivo estimation spectrum from among the plurality of in vivo estimation spectra.

The processor may extract a predetermined number of principal component spectra by analyzing the plurality of in vivo estimation spectra.

The processor may determine a correlation coefficient for each number of principal components by comparing the generated plurality of noise detection models with the plurality of concentration estimation models for each number of principal components, determine a number of principal components having a correlation coefficient which is less than or equal to a predetermined threshold value, or a correlation coefficient which has a greatest variation, extract a principal component spectrum, corresponding to the determined number of principal components, as the noise spectrum from among the predetermined number of principal component spectra, and extract a concentration estimation model, corresponding to the determined number of principal components, as the concentration estimation model for use in estimating the concentration of the analyte from among the plurality of concentration estimation models.

The processor may estimate the concentration of the analyte by using an in vivo spectrum, which is a more recently measured spectrum, from among the plurality of in vivo estimation spectra, and the updated concentration estimation model.

The analyte may be at least one of glucose, triglyceride, urea, uric acid, lactate, protein, cholesterol, or ethanol.

The processor may obtain a plurality of in vivo training spectra which are measured in a predetermined interval, and generate the plurality of concentration estimation models by varying a number of principal components based on the obtained plurality of in vivo training spectra.

The predetermined interval may be an interval in which the concentration of the analyte of an object is substantially constant.

According to an aspect of the disclosure, a method of estimating a concentration of an analyte may include obtaining an in vivo estimation spectrum, generating a plurality of noise detection models by varying a number of principal components based on in vivo spectra and the obtained in vivo estimation spectrum, comparing the generated plurality of noise detection models with a plurality of concentration estimation models for each number of principal components, extracting a noise spectrum and a concentration estimation model for use in estimating the concentration of the analyte based on the comparison, updating the extracted concentration estimation model based on the extracted noise spectrum, and estimating the concentration of the analyte by using the updated concentration estimation model and the obtained in vivo estimation spectrum.

The generating of the plurality of noise detection models by varying the number of principal components may include extracting a predetermined number of principal component spectra by analyzing all of the accumulated in vivo spectra or a predetermined number of the in vivo spectra, and the obtained in vivo estimation spectrum.

The extracting of the noise spectrum and the concentration estimation model for use in estimating the concentration of the analyte may include determining a correlation coefficient for each number of principal components by comparing the generated plurality of noise detection models with the plurality of concentration estimation models for each number of principal components, determining a number of principal components having a correlation coefficient which is less than or equal to a predetermined threshold value, or a correlation coefficient which has a greatest variation, extracting a principal component spectrum, corresponding to the determined number of principal components, as the noise spectrum from among the predetermined number of principal component spectra, and extracting a concentration estimation model, corresponding to the determined number of principal components, as the concentration estimation model for use in estimating the concentration of the analyte from among the plurality of concentration estimation models.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings and the detailed description, unless otherwise described, the same drawing reference numerals may refer to the same elements, features, and structures. The relative size and depiction of these elements may be exaggerated for clarity, illustration, and convenience.

DETAILED DESCRIPTION

Hereinafter, embodiments of the present disclosure will be described in detail with reference to the accompanying drawings. It should be noted that wherever possible, the same reference symbols refer to the same elements, features, and structures even in different drawings. In the following description, a detailed description of known functions and configurations incorporated herein may be omitted so as to not obscure the subject matter of the present disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, precedent, etc. Therefore, definitions of the terms should be made on the basis of the overall context of the disclosure.

It should be understood that, although the terms such as "first," "second," etc., may be used herein to describe various elements, these elements should not be limited by these terms. These terms may be used to distinguish one element from another. Any references to the singular forms of terms may include the plural forms of the terms unless expressly stated otherwise. In the present disclosure, it should be understood that the terms, such as "including," "having," etc., may indicate the existence of the features, numbers, steps, actions, components, parts, or combinations thereof, disclosed in the disclosure, and are not intended to preclude the possibility that one or more other features, numbers, steps, actions, components, parts, or combinations thereof, may exist or may be added.

Further, components that will be described in the disclosure may be discriminated merely according to functions mainly performed by the components. That is, two or more components may be integrated into a single component. Furthermore, a single component may be separated into two or more components. Moreover, each component may additionally perform some or all of a function executed by another component in addition to the main function thereof. Some or all of the main function of each component may be carried out by another component.

Figure 1:
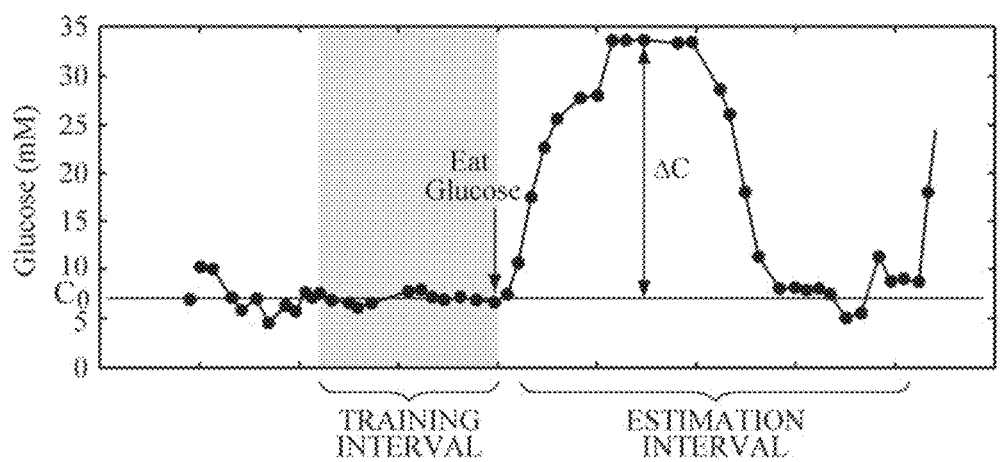
FIGS. 1 and 2 are diagrams explaining a concept of a Net Analyte Signal (NAS) algorithm according to an embodiment.
Figure 2:
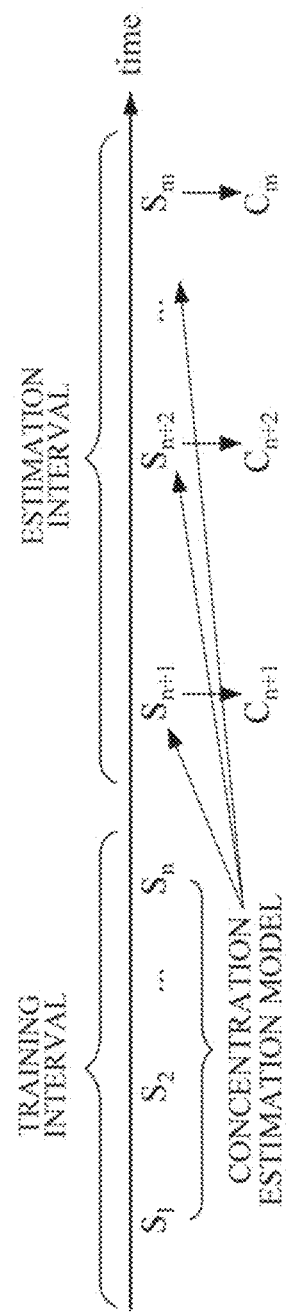

FIGS. 1 and 2 are diagrams explaining a concept of a Net Analyte Signal (NAS) algorithm.

Referring to FIGS. 1 and 2, the Net Analyte Signal (NAS) algorithm may generate an analyte concentration estimation model by identifying a spectrum change factor, which might not correspond to a change in an analyte concentration, using in spectra $S_1, S_2 \ldots,$ and $S_n$ measured in a training interval as training data. Further, the NAS algorithm may estimate analyte concentrations $C_{n+1}, C_{n+2}$ and $C_m$ by using in vivo spectra $S_{n+1} S_{n+2}, \ldots,$ and $S_m$ measured in an estimation interval following the training interval and the generated concentration estimation model. In this case, the training interval may be an interval (e.g., interval fasting interval if an analyte is glucose) in which the concentration of an in vivo analyte is substantially constant.

That is, the NAS algorithm generates a concentration estimation model based on the in vivo spectra measured in the training interval, and then estimates an analyte concentration by applying the generated concentration estimation model to the estimation interval. Accordingly, in the case where noise, which has not been identified, occurs during a training interval due to a factor such as a change of pressure between an object and an apparatus and the like, an error in estimating blood glucose may increase.

Figure 3:
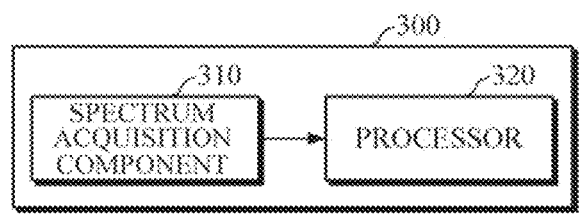
FIG. 3 is a block diagram illustrating an example of an apparatus for estimating a concentration of an analyte according to an embodiment.

FIG. 3 is a block diagram illustrating an example of an apparatus for estimating a concentration of an analyte. The concentration estimating apparatus 300 of FIG. 3 is an apparatus for estimating an analyte concentration by analyzing an in vivo spectrum of an object, and array be embedded in an electronic device or may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 3, the concentration estimating apparatus 300 includes a spectrum acquisition component 310 and a processor 320.

The spectrum acquisition component 310 may obtain in vivo spectra of an object. For example, the spectrum acquisition component 310 may obtain in vivo spectra (hereinafter referred to as "in vivo training spectra") which is measured in an interval in which an analyte concentration of an object is substantially constant (hereinafter referred to as a "training interval"), and/or in vivo spectra (hereinafter referred to as "in vivo estimation spectra") measured for estimating an analyte concentration of an object in an interval following the training interval (hereinafter referred to as an "estimation interval").

In an embodiment, the spectrum acquisition component 310 may obtain the in vivo spectra by receiving the in vivo spectra from an external device which measures and/or stores in vivo spectra. In this case, the spectrum acquisition component 310 may communicate with the external device by using various communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+communication, Wi-Fi communication, Radio Frequency Identification (RFID) communication, third generation (3G) communication, fourth generation (4G) communication, fifth generation (5G) communication, and the like.

In an embodiment, the spectrum acquisition component 310 may obtain in vivo spectra by directly measuring the in vivo spectra by emitting light toward an object and receiving light reflected by or scattered from the object. In this case, the spectrum acquisition component 310 may measure the in vivo spectra by using infrared spectroscopy, Raman spectroscopy, etc., but is not limited thereto, and may measure the in vivo spectra by using various other spectroscopic methods. To this end, the spectrum acquisition component 310 may include a light source which emits light toward an object, and a photodetector which measures in vivo spectra by receiving light reflected by or scattered from the object.

The light source may emit near infrared (NIR) light, mid infrared (MIR) light, and the like. However, wavelengths of light to be emitted by the light source may vary according to a purpose of measurement or the types of an analyte. Further, the light source may be formed as a single light-emitting body, or may be formed as an array of a plurality of light-emitting bodies. The light source may include a light emitting diode (LED), a laser diode, a fluorescent body, and the like.

The photodetector may include a photo diode, a photo transistor (PTr), a charge-coupled device (CCD), and the like. The photodetector may be formed as a single device, or may be formed as an array of a plurality of devices.

There may be various numbers and arrangements of light sources and photodetectors, and the number and arrangement thereof may vary according to the types and a purpose of use of an analyte, the size and shape of an electronic device in which the concentration estimating apparatus 300 is embedded, and the like.

The processor 320 may control the overall operation of the concentration estimating apparatus 300, and may include one or more processors, a memory, and a combination thereof.

At predetermined intervals or in response to a user's request, the processor 320 may control the spectrum acquisition component 310 to obtain the in vivo training spectra and/or the in vivo estimation spectra.

Once the spectrum acquisition component 310 obtains a plurality of in vivo training spectra, the processor 320 may generate a plurality of concentration estimation models by varying the number of principal components based on the obtained plurality of in vivo training spectra. In an embodiment, the processor 320 may generate a plurality of candidate concentration estimation models based on the NAS algorithm using the plurality of in vivo training spectra. In this case, examples of the analyte may include glucose, triglyceride, urea, uric acid, lactate, protein, cholesterol, ethanol, and the like, but the analyte is not limited thereto. In the case where an in vivo analyte is glucose, an analyte concentration may indicate a blood glucose level; and an interval in which an analyte is substantially constant may correspond to a fasting interval in which glucose is not consumed by an object.

After the plurality of concentration estimation models are generated, once the spectrum acquisition component 310 obtains the in vivo estimation spectra for use in estimating an analyte concentration, the processor 320 may determine a number of principal components by using the obtained in vivo estimation spectra, and may select a principal component spectrum corresponding to noise (hereinafter referred to as a "noise spectrum"), and a concentration estimation model for use in estimating the concentration. Further, the processor 320 may update the selected concentration estimation model by using the extracted noise spectrum, and may estimate the analyte concentration by using the updated concentration estimation model.

Hereinafter, examples of estimating an analyte concentration will be described in detail with reference to FIGS. 4 and 5.

Figure 4:
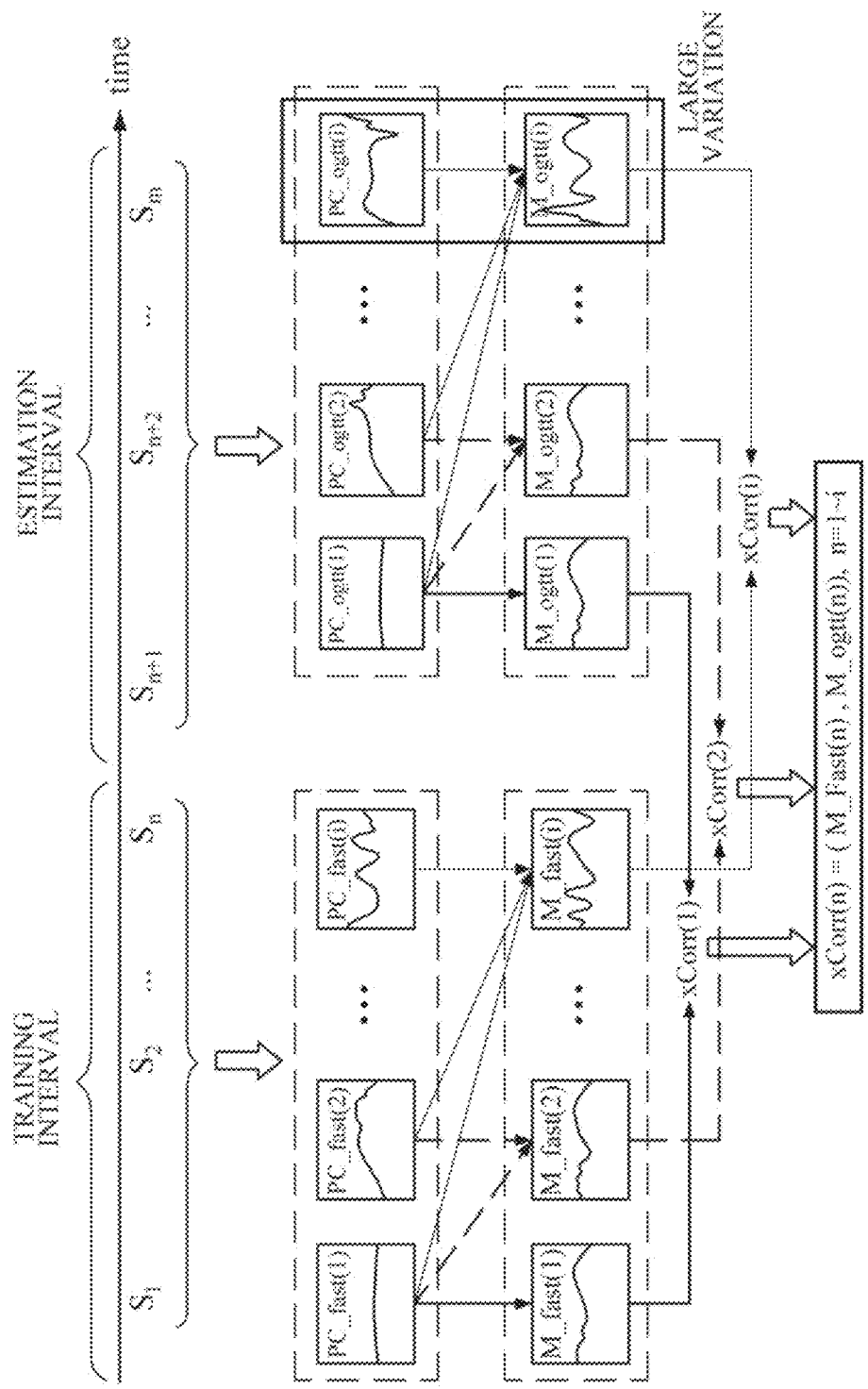
FIG. 4 is a diagram explaining an example of estimating a concentration of an analyte according to an embodiment.

FIG. 4 is a diagram explaining an example of estimating a concentration of an analyte.

Referring to FIGS. 3 and 4, the spectrum acquisition component 310 may obtain a plurality of in vivo training spectra S1, S2, ..., Sn which are measured in a training interval.

The processor 320 may extract number of principal component spectra PC_fast (1), PC_fast (2), ..., and PC_fast (i) by analyzing the plurality of in vivo training spectra S1, S2, ..., and Sn. For example, the processor 320 may extract the i number of principal component spectra PC_fast (1), PC_fast (2), ..., and PC_fast (i) from the plurality of in vivo training spectra S1, S2, ..., and Sn by using various dimension reduction algorithms such as Principal Component Analysis (PCA), Independent Component Analysis (ICA), Non-negative Matrix Factorization (NMF), Singular Value Decomposition (SVD), and the like.

The processor 320 may generate i number of concentration estimation models M_fast (1), M_fast (2), ..., and M_fast (i) by varying the number of principal components based on the extracted i number of principal component spectra PC_fast (1), PC_fast (2), ..., and PC_fast (i). For example, the processor 320 may generate the i number of concentration estimation models M_fast (1), M_fast (2), ..., and M_fast (i) by varying the number of principal components in such a manner that the processor 320 generates the concentration estimation model M_fast (1) by using one principal component spectrum PC_fast (1), and generates the concentration estimation model M_fast (2) by using two principal component spectra PC_fast (1) and PC_fast (2). In this case, the generated concentration estimation models may be represented by the following Equation 1.

$$M\_fast(i) = \begin{bmatrix} PC\_fast(1) \\ PC\_fast(2) \\ \vdots \\ PC\_fast(i) \\ \varepsilon g \end{bmatrix}^{-1} \quad [\text{Equation 1}]$$

Herein, $\varepsilon g$ denotes a spectrum of an analyte per unit concentration (e.g., 1 mM) (hereinafter referred to as a "pure component spectrum"), and may be obtained experimentally.

That is, upon varying the number of principal components, the processor 320 may obtain an inverse matrix of a matrix composed of the varied number of principal component spectra and the pure component spectrum of an analyte, to generate the plurality of concentration estimation models M_fast (1), M_fast (2), ..., and M_fast (i) for each number of principal components.

The spectrum acquisition component 310 may obtain a plurality of in vivo estimation spectra Sn+1, Sn+2, ..., and Sm which are measured in an estimation interval.

The processor 320 may extract i number of principal component spectra PC1_ogtt, PC2_ogtt, ..., and PCi_ogtt by analyzing the obtained plurality of in vivo estimation spectra Sn+1, Sn+2, ..., and Sm. For example, the processor 320 may extract the i number of principal component spectra PC1_ogtt, ..., and PCi_ogtt from the plurality of in vivo estimation spectra Sn+1, Sn+2, ..., and Sm by using various dimension reduction algorithms such as Principal Component Analysis (PCA), Independent Component Analysis (ICA), Non-negative Matrix Factorization (NMF), Singular Value Decomposition (SVD), and the like.

The processor 320 may generate i number of noise detection models M_ogtt(1), M_ogtt (2), ..., and M_ogtt (i) by varying the number of principal components based on the extracted i number of principal component spectra PC1_ogtt, PC2_ogtt, ..., and PCi_ogtt. For example, the processor 320 may generate the i number of noise detection models M_ogtt(1), M_ogtt(2), ..., and M_ogtt (i) by varying the number of principal components in such a manner that the processor 320 generates the noise detection model M_ogtt (1) by using one principal component spectrum PC1_ogtt, and generates the noise detection model M_ogtt(2) by using two principal component spectra PC1_ogtt and PC2_ogtt. In this case, the processor 320 may generate the noise detection models by using Equation 1 shown above.

The processor 320 may determine correlation coefficients for each number of principal components by comparing the plurality of concentration estimation models M_fast (1), M_fast (2), ..., and M_fast (i) with the plurality of noise detection models M_ogtt (1), M_ogtt (2), ..., and M_ogtt (i) for each number of principal components. For example, the processor 320 may determine correlation coefficients xCorr (1), xCorr (2), and xCorr (i) for each number of principal components in such a manner that the processor 320 determines a correlation coefficient xCorr (1) by comparing the concentration estimation model M_fast(1) with the noise detection model M_ogtt (1), and determines a correlation coefficient xCorr (2) by comparing the concentration estimation model M_fast (2) with the noise detection model M_ogtt (2).

The processor 320 may determine i number of principal components having a correlation coefficient which is less than or equal to a predetermined threshold value, or a correlation coefficient which has the greatest variation, and may add one to the determined i number of principal components to determine a number (i+1) of principal components (e.g., an optimal number, an improved nut fiber, etc.

In addition, the processor 320 may extract the principal component spectrum PCi_ogtt, which corresponds to the i number of principal components having a correlation coefficient which is less than or equal to a predetermined threshold value, or a correlation coefficient which has the largest variation, as a noise spectrum from among the i number of principal component spectra PC1_ogtt, PC2_ogtt, ..., and PCi_ogtt; and the processor 320 may extract the concentration estimation model M_fast (i), which corresponds to the i number of principal components having a correlation coefficient which is less than or equal to a predetermined threshold value, or a correlation coefficient which has the greatest variation, as a concentration estimation model for use in estimating an analyte concentration from among the plurality of concentration estimation models M_fast (1), M_fast (2), . . . , and M_fast(i).

The processor 320 may update the extracted concentration estimation model M_fast (i) by using the extracted noise spectrum PCi_ogtt. In this case, the updated concentration estimation model Mi_update may be represented by the following Equation 2.

$$\text{Mi\_update} = \begin{bmatrix} \text{PC\_fast}(1) \\ \text{PC\_fast}(2) \\ \vdots \\ \text{PC\_ogtt}(i) \\ \text{PC\_fast}(i) \\ \varepsilon g \end{bmatrix}^{-1} \quad [\text{Equation 2}]$$

That is, the processor 320 may generate the updated concentration estimation model Mi_update by adding the noise spectrum PCi_ogtt to the principal component spectra PC_fast (1), PC_fast (2), . . . , and PC_fast (i) used for generating the concentration estimation model M_fast (i), and by calculating an inverse matrix of a matrix composed of the principal component spectra PC_fast (1), PC_fast (2), . . . , and PC_fast (i), the noise spectrum PCi_ogtt, and the pure component spectrum of an analyte.

The processor 320 may select one of the plurality of in vivo estimation spectra Sn+1, Sn+2, . . . , and Sm, and may estimate an analyte concentration by using the selected in vivo spectrum and the updated concentration estimation model Mi_update. In an embodiment, the processor 320 may select the in vivo spectrum Sm, which is the last measured spectrum, from among the plurality of in vivo estimation spectra Sn+1, Sn+2, . . . , and Sm, but is not limited thereto.

For example, the processor 320 may estimate the analyte concentration by using the following Equation 3.

$$\begin{bmatrix} C1 \\ C2 \\ \vdots \\ Cnoise \\ Ci \\ Cg \end{bmatrix} = \begin{bmatrix} PC_{fast(1)} \\ PC_{fast(2)} \\ \vdots \\ PC_{ogtt(i)} \\ PC_{fast(i)} \\ \varepsilon g \end{bmatrix}^{-1} \times \frac{Sskin}{L} = Mi_{update} \times \frac{Sskin}{L} \quad [\text{Equation 3}]$$

Herein, C1, C2, and Ci denote the concentration of each principal component; Cnoise denotes the noise concentration; Cg denotes the analyte concentration; Sskin denotes the selected in vivo estimation spectrum; and L denotes a light path length.

Figure 5:
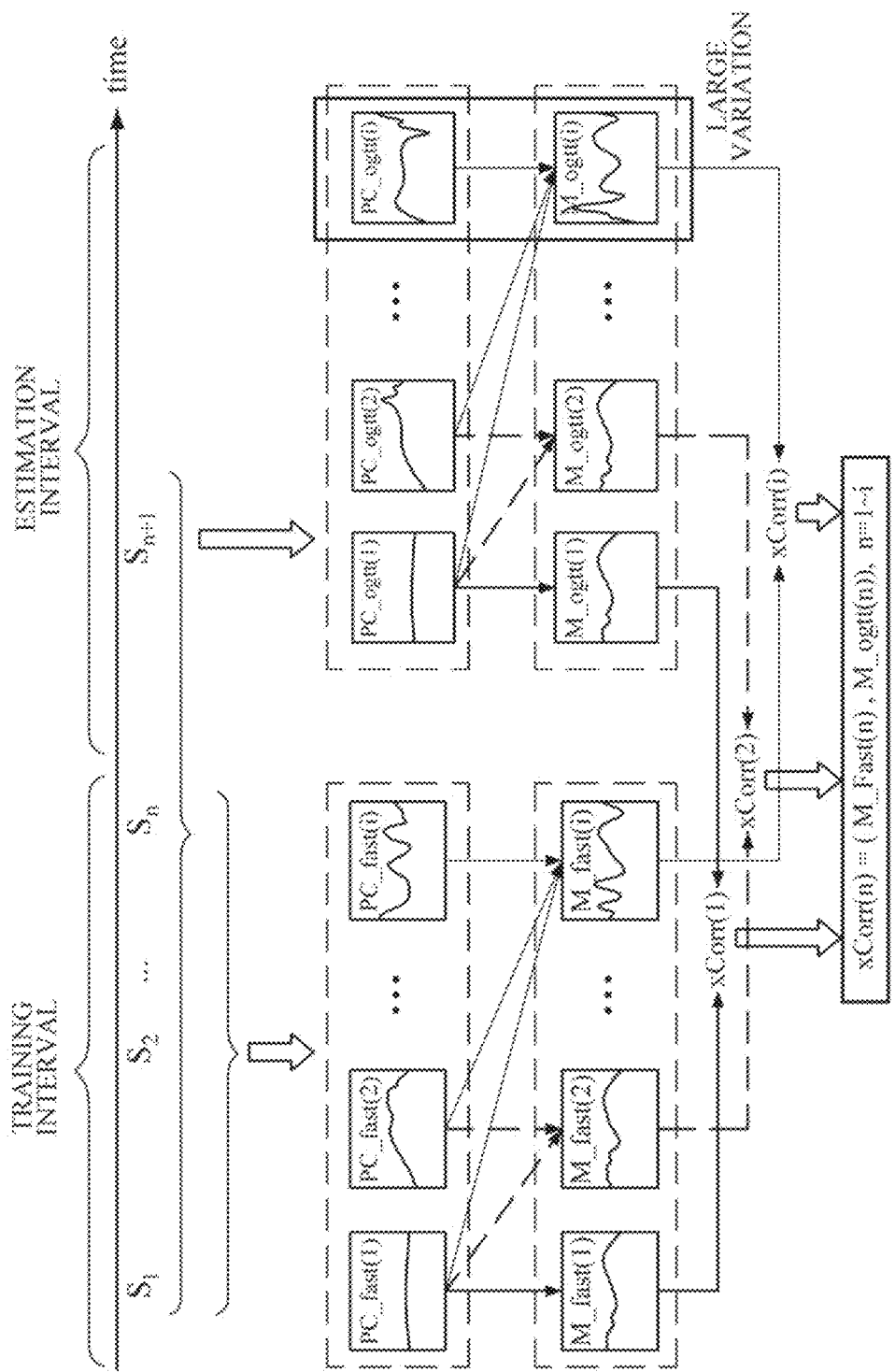
FIG. 5 is a diagram explaining another example of estimating a concentration of an analyte according to an embodiment.

FIG. 5 is a diagram explaining another example of estimating a concentration of an analyte.

Referring to FIGS. 3 and 5, the spectrum acquisition component 310 may obtain a plurality of in vivo training spectra S1, S2, . . . , and Sn which are measured in a training interval.

The processor 320 may extract number of principal component spectra PC_fast (1), PC_fast (2), . . . , and PC_fast (i) by analyzing the plurality of in vivo training spectra S1, S2, . . . , and Sn. For example, the processor 320 may extract the i number of principal component spectra PC_fast (1), PC_fast (2), . . . , and PC_fast (i) from the plurality of in vivo training spectra S1, S2, . . . , and Sn by using various dimension reduction algorithms such as Principal Component Analysis (PCA), Independent Component Analysis (ICA), Non-negative Matrix Factorization (NMF), Singular Value Decomposition (SVD), and the like.

The processor 320 may generate i number of concentration estimation models M_fast (1), M_fast (2), . . . , and M_fast (i) by varying the number of principal components based on the extracted i number of principal component spectra PC_fast (1), PC_fast (2), . . . , and PC_fast (i). For example, the processor 320 may generate the i number of concentration estimation models M_fast (1), M_fast(2), . . . , and M_fast (i) by varying the number of principal components in such a manner that the processor 320 generates the concentration estimation model M_fast (1) by using one principal component spectrum PC_fast (1), and generates the concentration estimation model M_fast (2) by using two principal component spectra PC_fast (1) and PC_fast (2). That is, upon varying the number of principal components, the processor 320 may calculate an inverse matrix of a matrix composed of the varied number of principal component spectra and the pure component spectrum of an analyte, to generate the plurality of concentration estimation models M_fast (1), M_fast (2), . . . , and M_fast (i) for each number of principal components.

The spectrum acquisition component 310 may obtain an in vivo estimation spectrum Sn+1 which is measured in an estimation interval.

The processor 320 may extract i number of principal component spectra PC1_ogtt, PC2_ogtt, . . . , and PCi_ogtt by analyzing all of the accumulated in vivo spectra S1, S2, . . . , and Sn or a predetermined number (k) of accumulated in vivo spectra Sn-k, Sn-k+1, . . . , and Sn, and the obtained in vivo estimation spectrum Sn+1. In this case, the processor 320 may use various dimension reduction algorithms such as Principal Component Analysis (PCA), Independent Component Analysis (ICA), Non-negative Matrix Factorization (NMF), Singular Value Decomposition (SVD), and the like. Further, the accumulated in vivo spectra may include the in vivo estimation spectra and the in vivo training spectra which are obtained before the spectrum acquisition component 310 obtains the in vivo estimation spectrum Sn+1.

The processor 320 may generate i number of noise detection models M_ogtt (1), M_ogtt (2), . . . , and M_ogtt (i) by varying the number of principal components based on the extracted i number of principal component spectra PC1_ogtt, PC2_ogtt, . . . , and PCi_ogtt. In this case, the processor 320 may generate the noise detection models by using Equation 1 shown above.

The processor 320 may determine correlation coefficients xCorr (1), xCorr (2), . . . , and xCorr (i) for each number of principal components by comparing the plurality of concentration estimation models M_fast (1), M_fast (2), . . . , and M_fast (i) with the plurality of noise detection models M_ogtt (1), M_ogtt (2), . . . , and M_ogtt (i) for each number of principal components.

The processor 320 may determine i number of principal components having a correlation coefficient which is less than or equal to a predetermined threshold value, or a correlation coefficient which has the greatest variation, and may add one to the determined i number of principal components to determine a number (i+1) of principal components (e.g., an optimal number).

In addition, the processor 320 may extract the principal component spectrum PCi_ogtt, which corresponds to the i number of principal components having a correlation coefficient which is less than or equal to a predetermined threshold value, or a correlation coefficient which has the greatest variation, as a noise spectrum from among the i number of principal component spectra PC1_ogtt, PC2_ogtt, . . . , and PCi_ogtt; and the processor 320 may extract the concentration estimation model M_fast (i), which corresponds to the i number of principal components having a correlation coefficient which is less than or equal to a predetermined threshold value, or a correlation coefficient which has the largest variation, as a concentration estimation model for use in estimating an analyte concentration from among the plurality of concentration estimation models M_fast (1), M_fast (2), . . . , and M_fast (i).

The processor 320 may update the extracted concentration estimation model M_fast (i) by using the extracted noise spectrum PCi_ogtt. For example, the processor 320 may generate the updated concentration estimation model Mi_update by adding the noise spectrum PCi_ogtt to the principal component spectra PC_fast (1), PC_fast (2), . . . , and PC_fast (i) used for generating the concentration estimation model M_fast (i), and by calculating an inverse matrix of a matrix composed of the principal component spectra PC_fast (1), PC_fast (2), . . . , and PC_fast (i), the noise spectrum PCi_ogtt, and the pure component spectrum of an analyte. The updated concentration estimation model may be represented by Equation 2 shown above.

The processor 320 may estimate an analyte concentration by using the in vivo estimation spectrum Sn+1 and the updated concentration estimation model Mi_update. In this case, the processor 320 may estimate the analyte concentration by using Equation 3 shown above.

Figure 6:
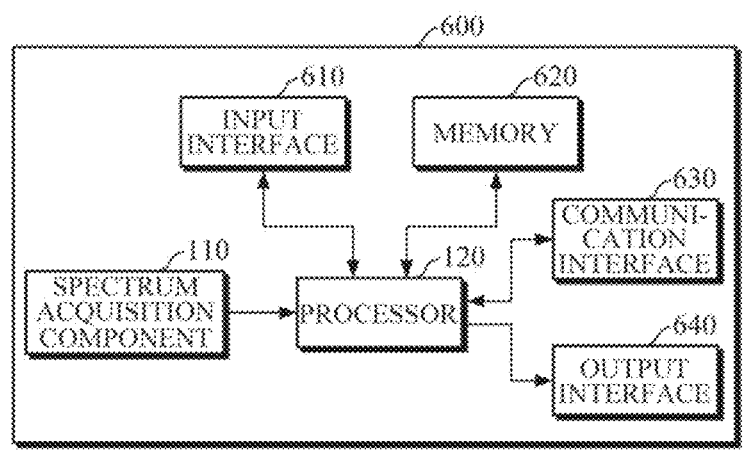
FIG. 6 is a block diagram illustrating another example of an apparatus for estimating a concentration of an analyte according to an embodiment.

FIG. 6 is a block diagram illustrating another example of an apparatus for estimating a concentration of an analyte. The concentration estimating apparatus 600 of FIG. 6 is an apparatus for estimating an analyte concentration by analyzing in vivo spectra of an object, and may be embedded in an electronic device or may be enclosed in a housing to be provided as a separate device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 6, the concentration estimating apparatus 600 includes the spectrum acquisition component 110, the processor 120, an input interface 610, a memory 620, a communication interface 630, and an output interface 640. Here, the spectrum acquisition component 110 and the processor 120 may be substantially similar to the spectrum acquisition component 310 and the processor 320 described above with reference to FIGS. 3 to 5, such that detailed description thereof may be omitted.

The input interface 610 may receive input of various operation signals from a user. In an embodiment, the input interface 610 may include a keypad, a dome switch, a touch pad (e.g., static pressure touch pad, a capacitive touch pad, and the like), a jog wheel, a jog switch, a hardware (H/W) button, and the like. Particularly, the touch pad, which forms a layer structure with a display, may be referred to as a touch screen.

The memory 620 may store programs or instructions for operation of the concentration estimating apparatus 600, data input to and output from the concentration estimating apparatus 600, and data processed by the concentration estimating apparatus 600. In addition, the memory 620 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the concentration estimating apparatus 600 may communicate with an external storage medium, such as web storage and the like, which performs a storage function of the memory 620 via the Internet.

The communication interface 630 may perform communication with an external device. For example, the communication interface 630 may transmit, to the external device, the data input to the concentration estimating apparatus 600, the data stored in and processed by the concentration estimating apparatus 600 and the like, or may receive, from the external device, various data for estimating an analyte concentration in blood.

In this case, the external device may be medical equipment using the data input to the concentration estimating apparatus 600, the data stored in and processed by the concentration estimating apparatus 600, and the like, a printer to print out results, or a display to display the results. In addition, the external device may be a digital television (TV), a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 630 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, Wi-Fi communication, Radio Frequency Identification (RFID) communication, 3G communication, 4G communication, 5G communication, and the like. However, this is merely exemplary and is not intended to be limiting.

The output interface 640 may output the data input to the concentration estimating apparatus 600, the data stored in and processed by the concentration estimating apparatus 600, and the like. In an embodiment, the output interface 640 may output the data input to the concentration estimating apparatus 600, the data stored in and processed by the concentration estimating apparatus 600, and the like, by using at least one of an acoustic method, a visual method, and a tactile method. To this end, the output interface 640 may include a display, a speaker, a vibrator, and the like.

Figure 7:
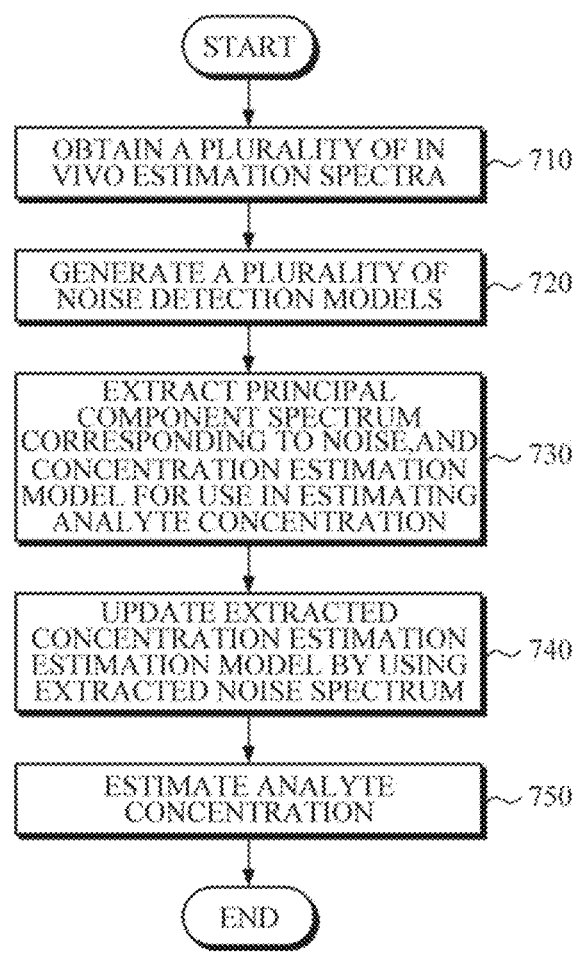
FIG. 7 is a flowchart illustrating an example of a method of estimating a concentration of an analyte according to an embodiment.

FIG. 7 is a flowchart illustrating an example of a method of estimating a concentration of an analyte. The concentration estimating method of FIG. 7 may be performed by the concentration estimating apparatuses 300 or 600 of FIG. 3 or 6.

Referring to FIG. 7, the concentration estimating apparatus may obtain a plurality of in vivo estimation spectra which are measured in an estimation interval in operation 710. For example, the concentration estimating apparatus may obtain the plurality of in vivo estimation spectra by receiving the in vivo estimation spectra from an external device which measures and/or stores in vivo spectra, or by directly measuring the in vivo estimation spectra by emitting light toward an object and receiving light reflected by or scattered from the object.

The concentration estimating apparatus may generate a plurality of noise detection models by varying the number of principal components based on the obtained plurality of in vivo estimation spectra in operation 720. For example, the concentration estimating apparatus may extract a predetermined number of principal component spectra by analyzing the obtained plurality of in vivo estimation spectra, and may generate the plurality of noise detection models by varying the number of principal components based on the extracted predetermined number of principal component spectra. For example, the concentration estimating apparatus may extract the predetermined number of principal component spectra from the plurality of in vivo estimation spectra by using various dimension reduction algorithms such as Principal Component Analysis (PCA), Independent Component Analysis (ICA), Non-negative Matrix Factorization (NMF), Singular Value Decomposition (SVD), and the like; and may generate the plurality of noise detection models by varying the number of principal components using Equation 1 shown above.

The concentration estimating apparatus may compare the plurality of noise detection models with a plurality of pre-stored concentration estimation models; and based on the comparison, the concentration estimating apparatus may extract a principal component spectrum corresponding to noise, and a concentration estimation model for use in estimating an analyte concentration in operation 730. For example, the concentration estimating apparatus may determine correlation coefficients for each number of principal components by comparing the plurality of concentration estimation models with the plurality of noise detection models for each number of principal components. Further, the concentration estimating apparatus may determine a number of principal components having a correlation coefficient which is less than or equal to a predetermined threshold value, or a correlation coefficient which has the greatest variation, d the concentration estimating apparatus may extract a principal component spectrum, corresponding to the determined number of principal components, as the noise spectrum from among the predetermined number of principal component spectra extracted from the plurality of in vivo estimation spectra, and the concentration estimating apparatus may extract a concentration estimation model, corresponding to the determined number of principal components, as the concentration estimation model for use in estimating an analyte concentration from among the plurality of concentration estimation models. In this case, the concentration estimating apparatus may add one to the determined number of principal components to determine a number of principal components (e.g., an optimal number).

The concentration estimating apparatus may update the extracted concentration estimation model by using the extracted noise spectrum in operation 740. For example, the concentration estimating apparatus may generate the updated concentration estimation model by adding the extracted noise spectrum to the principal component spectra used for generating the extracted concentration estimation model, and by calculating an inverse matrix of a matrix composed of the principal component spectra used for generating the extracted concentration estimation model, the extracted noise spectrum, and the pure component spectrum of an analyte. In this case, the updated concentration estimation model may be represented by Equation 2 shown above.

The concentration estimating apparatus may estimate an analyte concentration by using one of the plurality of in vivo estimation spectra and the updated concentration estimation model in operation 750. In an embodiment, the concentration estimating apparatus may select an in vivo spectrum, which is the last measured spectrum, from among the plurality of in vivo estimation spectra, and may estimate the analyte concentration by using the selected in vivo spectrum and Equation 3 shown above.

Figure 8:
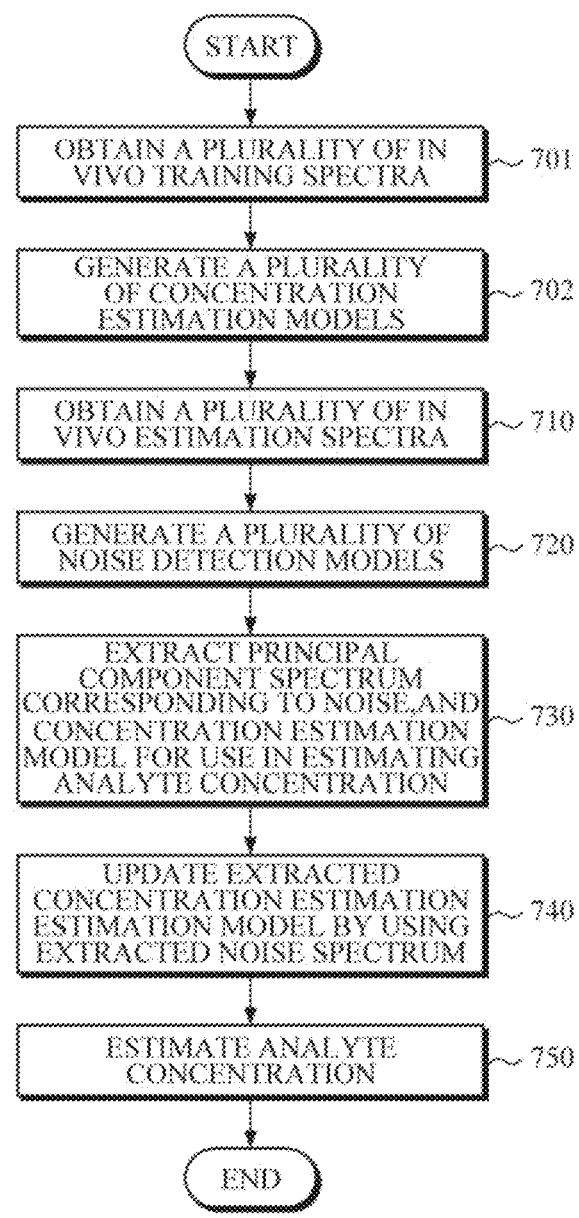
FIG. 8 is a flowchart illustrating another example of a method of estimating a concentration of an analyte according to an embodiment.

FIG. 8 is a flowchart illustrating another example of a method of estimating a concentration of an analyte. The concentration estimation method of FIG. 8 may be performed by the concentration estimating apparatuses 300 or 600 of FIG. 3 or 6. The operations 710, 720, 730, 740, and 750 of FIG. 8 may be substantially similar to operations 710, 720, 730, 740, and 750 described above with reference to FIG. 7, such that detailed description thereof may be omitted.

Referring to FIG. 8, the concentration estimating apparatus may obtain a plurality of in vivo training spectra which are measured in a training interval in operation 701. For example, the concentration estimating apparatus may obtain the plurality of in vivo training spectra by receiving the in vivo training spectra from an external device which measures and/or stores in vivo spectra, or by directly measuring the in vivo training spectra by emitting light toward an object and receiving light reflected by or scattered from the object.

The concentration estimating apparatus may generate a plurality of concentration estimation models by varying the number of principal components based on the obtained plurality of in vivo training spectra in operation 702. For example, the concentration estimating apparatus may extract a predetermined number of principal component spectra by analyzing the obtained plurality of in vivo training spectra, and may generate the plurality of concentration estimation models by varying the number of principal components based on the extracted predetermined number of principal component spectra. For example, the concentration estimating apparatus may extract the predetermined number of principal component spectra from the plurality of in vivo training spectra by using various dimension reduction algorithms such as Principal Component Analysis (PCA), Independent Component Analysis (ICA), Non-negative Matrix Factorization (NMF), Singular Value Decomposition (SVD), and the like; and the concentration estimating apparatus may generate the plurality of concentration estimation models by varying the number of principal components using the above Equation 1.

Figure 9:
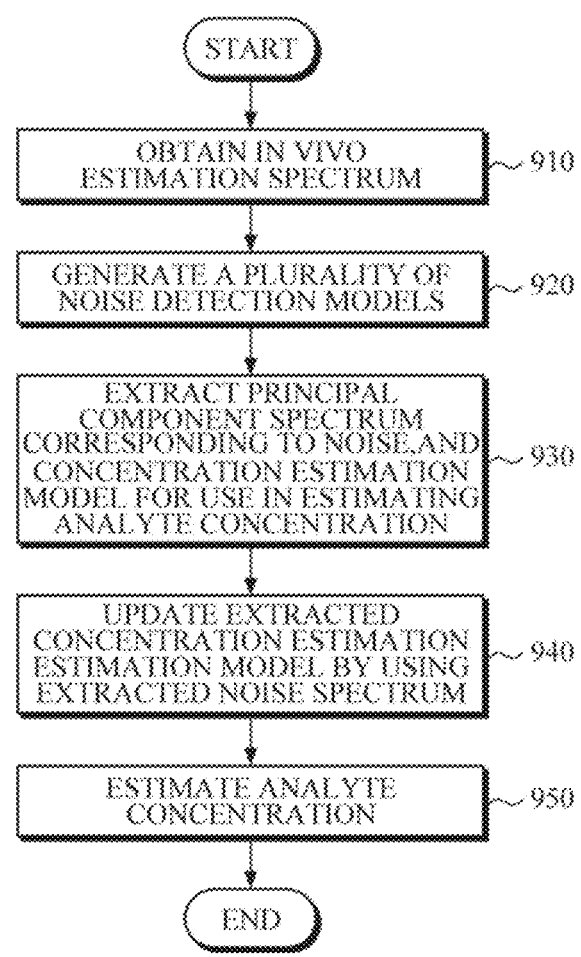
FIG. 9 is a flowchart illustrating yet another example of a method of estimating a concentration of an analyte according to an embodiment.

FIG. 9 is a flowchart illustrating yet another example of a method of estimating a concentration of an analyte. The concentration estimation method of FIG. 9 may be performed by the concentration estimating apparatuses 300 or 600 of FIG. 3 or 6.

Referring to FIG. 9, the concentration estimating apparatus may obtain an in vivo estimation spectrum which is measured in an estimation interval in operation 910. For example, the concentration estimating apparatus may obtain the in vivo estimation spectrum by receiving the in vivo estimation spectrum from an external device which measures and/or stores in vivo spectra, or by directly measuring the in vivo estimation spectrum by emitting light toward an object and receiving light reflected by or scattered from the object.

The concentration estimating apparatus may generate a plurality of noise detection models by varying the number of principal components based on all of the accumulated in vivo spectra or a predetermined number of accumulated in vivo spectra, and the obtained in vivo estimation spectrum in operation 920. For example, the concentration estimating apparatus may extract a predetermined number of principal component spectra by analyzing all of the accumulated in vivo spectra or the predetermined number of accumulated in vivo spectra, and the obtained in vivo estimation spectrum, and may generate the plurality of noise detection models by varying the number of principal components based on the extracted predetermined number of principal component spectra.

The concentration estimating apparatus may compare the plurality of noise detection models with a plurality of pre-stored concentration estimation models; and based on the comparison, the concentration estimating apparatus may extract a principal component spectrum corresponding to noise, and a concentration estimation model for use in estimating an analyte concentration in operation 930. For example, the concentration estimating apparatus may determine correlation coefficients for each number of principal components by comparing the plurality of concentration estimation models with the plurality of noise detection models for each number of principal components. Further, the concentration estimating apparatus may determine a number of principal components having a correlation coefficient which is less than or equal to a predetermined threshold value, or a correlation coefficient which has the greatest variation; and the concentration estimating apparatus may extract a principal component spectrum, corresponding to the determined number of principal components, as the noise spectrum from among the extracted predetermined number of principal component spectra, and the concentration estimating apparatus may extract a concentration estimation model, corresponding to the determined number of principal components, as the concentration estimation model for use in estimating an analyte concentration from among the plurality of concentration estimation models. In this case, the concentration estimating apparatus may add one to the determined number of principal components to determine a number of principal components (e.g., an optimal number).

The concentration estimating apparatus may update the extracted concentration estimation model by using the extracted noise spectrum in operation 940. For example, the concentration estimating apparatus may generate the updated concentration estimation model by adding the extracted noise spectrum to the principal component spectra used for generating the extracted concentration estimation model, and by calculating an inverse matrix of a matrix composed of the principal component spectra used for generating the extracted concentration estimation model, the extracted noise spectrum, and the pure component spectrum of an analyte. In this case, the updated concentration estimation model may be represented by Equation 2 shown above.

The concentration estimating apparatus may estimate an analyte concentration by using the obtained in vivo estimation spectra and the updated concentration estimation model in operation 950. In an embodiment, the concentration estimating apparatus may estimate the analyte concentration by using Equation 3 shown above.

Figure 10:
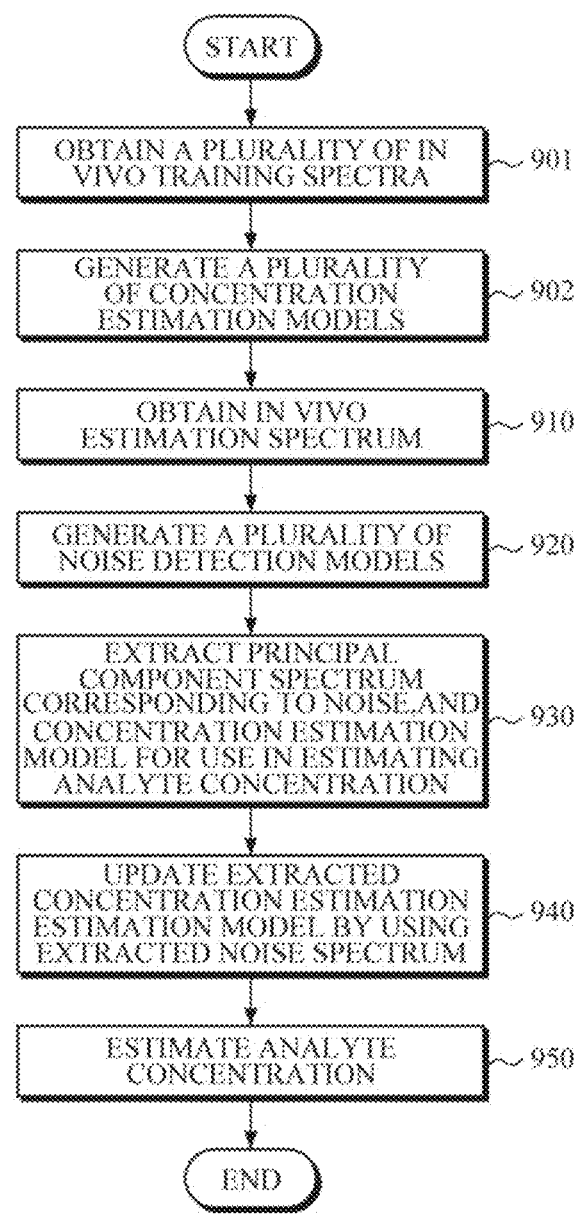
FIG. 10 is a flowchart illustrating still another example of a method of estimating a concentration of an analyte according to an embodiment.

FIG. 10 is a flowchart illustrating still another example of a method of estimating a concentration of an analyte. The concentration estimation method of FIG. 10 may be performed by the concentration estimating apparatuses 300 or 600 of FIG. 3 or 6. The operations 910, 920, 930, 940, and 950 of FIG. 10 may be substantially similar to operations 910, 920, 930, 940, and 950 described above with reference to FIG. 9, such that detailed description thereof may be omitted.

Referring to FIG. 10, the concentration estimating apparatus may obtain a plurality of in vivo training spectra which are measured in a training interval in operation 901. For example, the concentration estimating apparatus may obtain the plurality of in vivo training spectra by receiving the in vivo training spectra from an external device which measures and/or stores in vivo spectra, or by directly measuring the in vivo training spectra by emitting light toward an object and receiving light reflected by or scattered from the object.

The concentration estimating apparatus may generate a plurality of concentration estimation models by varying the number of principal components based on the obtained plurality of in vivo training spectra in operation 902. For example, the concentration estimating apparatus may extract a predetermined number of principal component spectra by analyzing the obtained plurality of in vivo training spectra, and may generate the plurality of concentration estimation models by varying the number of principal components based on the extracted predetermined number of principal component spectra.

Figure 11:
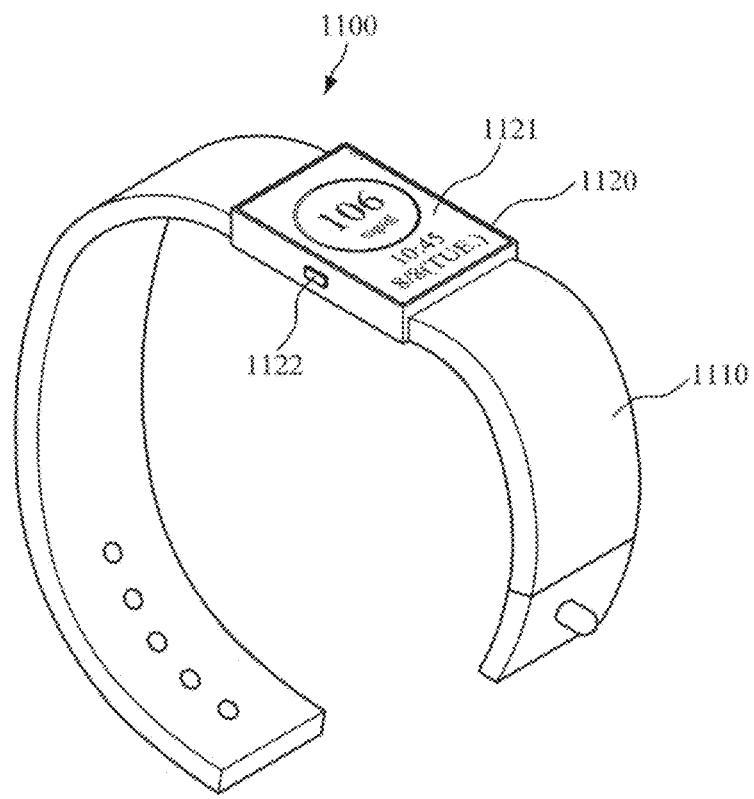
FIG. 11 is a diagram illustrating an example of a wrist-type wearable device according to an embodiment.

FIG. 11 is a diagram illustrating an example of a wrist-type wearable device.

Referring to FIG. 11, the wrist-type wearable device 1100 includes a strap 1110 and a main body 1120.

The strap 1110 may be connected to both ends of the main body 1120 so as to be fastened in a detachable manner or may be integrally formed therewith as a smart band. The strap 1110 may be made of a flexible material to be wrapped around a user's wrist so that the main body 1120 may be worn on the wrist.

The main body 1120 may include the aforementioned concentration estimating apparatuses 300 and 600. Further, the main body 1120 may include a battery which supplies power to the wrist-type wearable device 1100 and the concentration estimating apparatuses 300 and 600.

An optical sensor may be mounted at the bottom of the main body 1120 to be exposed to a user's wrist. Accordingly, when a user wears the wrist-type wearable device 1100, the optical sensor may naturally come into contact with the user's skin. In this case, the optical sensor may obtain in vivo spectra by emitting light toward an object and receiving light reflected by or scattered from the object.

The wrist-type wearable device 1100 may further include a display 1121 and an input interface 1122 which are mounted on the main body 1120. The display 1121 may display data processed by the wrist-type wearable device 1100 and the concentration estimating apparatuses 300 and 600, processing result data thereof, and the like. The input interface 1122 may receive various operation signals from a user.

The present disclosure can be realized as computer-readable code stored on a non-transitory computer-readable medium. The computer-readable medium may be any type of recording device in which data is stored in a computer-readable manner. Examples of the computer-readable recording medium include a ROM, a RAM, a CD-ROM, a magnetic tape, a floppy disc, an optical data storage, and a carrier wave (e.g., data transmission through the Internet). The computer-readable recording medium may be distributed over a plurality of computer systems connected to a network so that computer-readable code is written thereto and executed therefrom in a decentralized manner.

The present disclosure has been described herein with regard to various embodiments. However, it will be obvious to those skilled in the art that various changes and modifications can be made without departing from the technical spirit of the present disclosure. Thus, it is clear that the above-described embodiments are illustrative in all aspects and are not intended to limit the present disclosure.

What is claimed is:

1. A method of estimating a concentration of an analyte, the method comprising:
    obtaining a plurality of in vivo estimation spectra;
    generating a plurality of noise detection models by varying a number of principal components from among the plurality of in vivo estimation spectra;
    comparing the generated plurality of noise detection models with a plurality of concentration estimation models for each number of principal components, wherein each of the plurality of concentration estimation models uses a different number of principal components than another of the concentration estimation models;
    extracting a noise spectrum and a concentration estimation model for use in estimating the concentration of the analyte based on the comparison;
    updating the extracted concentration estimation model based on the extracted noise spectrum; and
    estimating the concentration of the analyte by using the updated concentration estimation model and an in vivo estimation spectrum from among the plurality of in vivo estimation spectra,
    wherein the extracting of the noise spectrum and the concentration estimation model for use in estimating the concentration of the analyte comprises:
    determining a correlation coefficient for each number of principal components by comparing the generated plurality of noise detection models with the plurality of concentration estimation models for each number of principal component.

2. The method of claim 1, wherein the obtaining of the plurality of in vivo estimation spectra comprises obtaining the in vivo estimation spectra by receiving the plurality of in vivo estimation spectra from an external device, or by measuring the plurality of in vivo estimation spectra by emitting light towards an object and receiving light reflected by or scattered from the object.

3. The method of claim 1, wherein the generating of the plurality of noise detection models by varying the number of principal components comprises extracting a predetermined number of principal component spectra by analyzing the plurality of in vivo estimation spectra.

4. The method of claim 3, wherein the extracting of the predetermined number of principal component spectra comprises extracting the predetermined number of principal component spectra by using one of Principal Component Analysis (PCA), Independent Component Analysis (ICA), Non-negative Matrix Factorization (NMF), and Singular Value Decomposition (SVD).

5. The method of claim 3, wherein the extracting of the noise spectrum and the concentration estimation model for use in estimating the concentration of the analyte further comprises:
    determining a number of principal components having a correlation coefficient which is less than or equal to a predetermined threshold value, or a correlation coefficient which has a greatest variation;
    extracting a principal component spectrum, corresponding to the determined number of principal components, as the noise spectrum from among the predetermined number of principal component spectra; and
    extracting a concentration estimation model, corresponding to the determined number of principal components, as the concentration estimation model for use in estimating the concentration of the analyte from among the plurality of concentration estimation models.

6. The method of claim 1, wherein the estimating of the concentration of the analyte comprises selecting an in vivo spectrum, which is a most recently measured spectrum compared with other obtained spectra, from among the plurality of in vivo estimation spectra.

7. The method of claim 1, wherein the analyte is at least one of glucose, triglyceride, urea, uric acid, lactate, protein, cholesterol, or ethanol.

8. The method of claim 1, further comprising:
    obtaining a plurality of in vivo training spectra which are measured in a predetermined interval; and
    generating the plurality of concentration estimation models by varying a number of principal components based on the obtained plurality of in vivo training spectra.

9. The method of claim 8, wherein the predetermined interval is an interval in which the concentration of the analyte of an object is substantially constant.

10. The method of claim 9, wherein:
    the analyte is glucose; and
    the interval, in which the concentration of the analyte of the object is substantially constant, is a fasting interval.

11. An apparatus for estimating a concentration of an analyte, the apparatus comprising:
    a processor configured to:
        obtain a plurality of in vivo estimation spectra;
        generate a plurality of noise detection models by varying a number of principal components from among the plurality of in vivo estimation spectra;
        compare the generated plurality of noise detection models with a plurality of concentration estimation models for each number of principal components, wherein each of the plurality of concentration estimation models uses a different number of principal components than another of the concentration estimation models;
        extract a noise spectrum and a concentration estimation model for use in estimating the concentration of the analyte based on the comparison;

update the extracted concentration estimation model based on the extracted noise spectrum; and
estimate the concentration of the analyte by using the updated concentration estimation model and an in vivo estimation spectrum from among the plurality of in vivo estimation spectra,
wherein the processor is configured to:
determine a correlation coefficient for each number of principal components by comparing the generated plurality of noise detection models with the plurality of concentration estimation models for each number of principal components.

12. The apparatus of claim 11, wherein the processor is configured to extract a predetermined number of principal component spectra by analyzing the plurality of in vivo estimation spectra.

13. The apparatus of claim 12, wherein the processor is further configured to:
determine a number of principal components having a correlation coefficient which is less than or equal to a predetermined threshold value, or a correlation coefficient which has a greatest variation;
extract a principal component spectrum, corresponding to the determined number of principal components, as the noise spectrum from among the predetermined number of principal component spectra; and
extract a concentration estimation model, corresponding to the determined number of principal components, as the concentration estimation model for use in estimating the concentration of the analyte from among the plurality of concentration estimation models.

14. The apparatus of claim 11, wherein the processor is configured to estimate the concentration of the analyte by using an in vivo spectrum, which is a more recently measured spectrum compared with other obtained spectra, from among the plurality of in vivo estimation spectra, and the updated concentration estimation model.

15. The apparatus of claim 11, wherein the analyte is at least one of glucose, triglyceride, urea, uric acid, lactate, protein, cholesterol, or ethanol.

16. The apparatus of claim 11, wherein:
the processor is configured to:
obtain a plurality of in vivo training spectra which are measured in a predetermined interval; and
generate the plurality of concentration estimation models by varying a number of principal components based on the obtained plurality of in vivo training spectra.

17. The apparatus of claim 16, wherein the predetermined interval is an interval in which the concentration of the analyte of an object is substantially constant.

18. A method of estimating a concentration of an analyte, the method comprising:
obtaining an in vivo estimation spectrum;
generating a plurality of noise detection models by varying a number of principal components based on in vivo spectra and the obtained in vivo estimation spectrum;
comparing the generated plurality of noise detection models with a plurality of concentration estimation models for each number of principal components, wherein each of the plurality of concentration estimation models uses a different number of principle components than another of the concentration estimation models;
extracting a noise spectrum and a concentration estimation model for use in estimating the concentration of the analyte based on the comparison;
updating the extracted concentration estimation model based on the extracted noise spectrum; and
estimating the concentration of the analyte by using the updated concentration estimation model and the obtained in vivo estimation spectrum,
wherein the extracting of the noise spectrum and the concentration estimation model for use in estimating the concentration of the analyte comprises:
determining a correlation coefficient for each number of principal components by comparing the generated plurality of noise detection models with the plurality of concentration estimation models for each number of principal components.

19. The method of claim 18, wherein the generating of the plurality of noise detection models by varying the number of principal components comprises extracting a predetermined number of principal component spectra by analyzing all of the in vivo spectra or a predetermined number of the in vivo spectra, and the obtained in vivo estimation spectrum.

20. The method of claim 19, wherein the extracting of the noise spectrum and the concentration estimation model for use in estimating the concentration of the analyte further comprises:
determining a number of principal components having a correlation coefficient which is less than or equal to a predetermined threshold value, or a correlation coefficient which has a greatest variation;
extracting a principal component spectrum, corresponding to the determined number of principal components, as the noise spectrum from among the predetermined number of principal component spectra; and
extracting a concentration estimation model, corresponding to the determined number of principal components, as the concentration estimation model for use in estimating the concentration of the analyte from among the plurality of concentration estimation models.

* * * * *